(12) United States Patent
Williams et al.

(10) Patent No.: US 9,403,753 B2
(45) Date of Patent: Aug. 2, 2016

(54) DUAL SITE CATALYST FOR MILD, SELECTIVE NITRILE REDUCTION

(71) Applicant: University of Southern California, Los Angeles, CA (US)

(72) Inventors: Travis J. Williams, Los Angeles, CA (US); Zhiyao Lu, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 14/948,898

(22) Filed: Nov. 23, 2015

(65) Prior Publication Data

US 2016/0145193 A1   May 26, 2016

Related U.S. Application Data

(60) Provisional application No. 62/082,992, filed on Nov. 21, 2014.

(51) Int. Cl.
| | |
|---|---|
| *C07F 15/00* | (2006.01) |
| *C07D 213/00* | (2006.01) |
| *C07C 209/00* | (2006.01) |
| *C07C 209/48* | (2006.01) |
| *B01J 31/18* | (2006.01) |
| *C07C 213/02* | (2006.01) |
| *C07D 213/38* | (2006.01) |
| *C07D 307/68* | (2006.01) |
| *C07D 333/38* | (2006.01) |

(52) U.S. Cl.
CPC ............ *C07C 209/48* (2013.01); *B01J 31/181* (2013.01); *C07C 213/02* (2013.01); *C07D 213/38* (2013.01); *C07D 307/68* (2013.01); *C07D 333/38* (2013.01); *C07F 15/0046* (2013.01); *B01J 2231/64* (2013.01); *B01J 2531/821* (2013.01)

(58) Field of Classification Search
CPC .. C07C 209/48; C07C 213/02; C07D 213/38; C07D 333/38; C07D 307/68; C07F 15/0046; B01J 31/181
USPC ................. 546/329; 548/109; 549/72, 487; 564/375, 385
See application file for complete search history.

(56) References Cited

PUBLICATIONS

Lu et al., Chemical Communications, vol. 50, pp. 5391-5393 (Published online Dec. 24, 2013).*

* cited by examiner

*Primary Examiner* — Porfirio Nazario Gonzalez
(74) *Attorney, Agent, or Firm* — Brooks Kushman P.C.

(57) ABSTRACT

A ruthenium bis(pyrazolyl)borate scaffold that enables cooperative reduction reactivity in which boron and ruthenium centers work in concert to effect selective nitrile reduction is provided. The pre-catalyst compound $[\kappa^3\text{-}(1\text{-pz})_2\text{HB}(N{=}CHCH_3)]Ru(cymene)^+$ $TfO^-$ (pz=pyrazolyl) was synthesized using readily-available materials through a straightforward route, thus making it an appealing catalyst for a number of reactions.

20 Claims, 4 Drawing Sheets

DUAL SITE CATALYST FOR MILD, SELECTIVE NITRILE REDUCTION

CROSS-REFERENCE TO RELATED APPLICATIONS

This application claims the benefit of U.S. provisional application Ser. No. 62/082,992 filed Nov. 21, 2014, the disclosure of which is hereby incorporated in its entirety by reference herein.

STATEMENT REGARDING FEDERALLY SPONSORED RESEARCH OR DEVELOPMENT USE

The invention was made with Government support under Contract No. CHE-1054910 (and others) awarded by the National Science Foundation. The Government has certain rights to the invention.

TECHNICAL FIELD

In at least one aspect, the present invention is related to catalysts for reducing nitriles and other functional groups.

BACKGROUND

Figure 1:
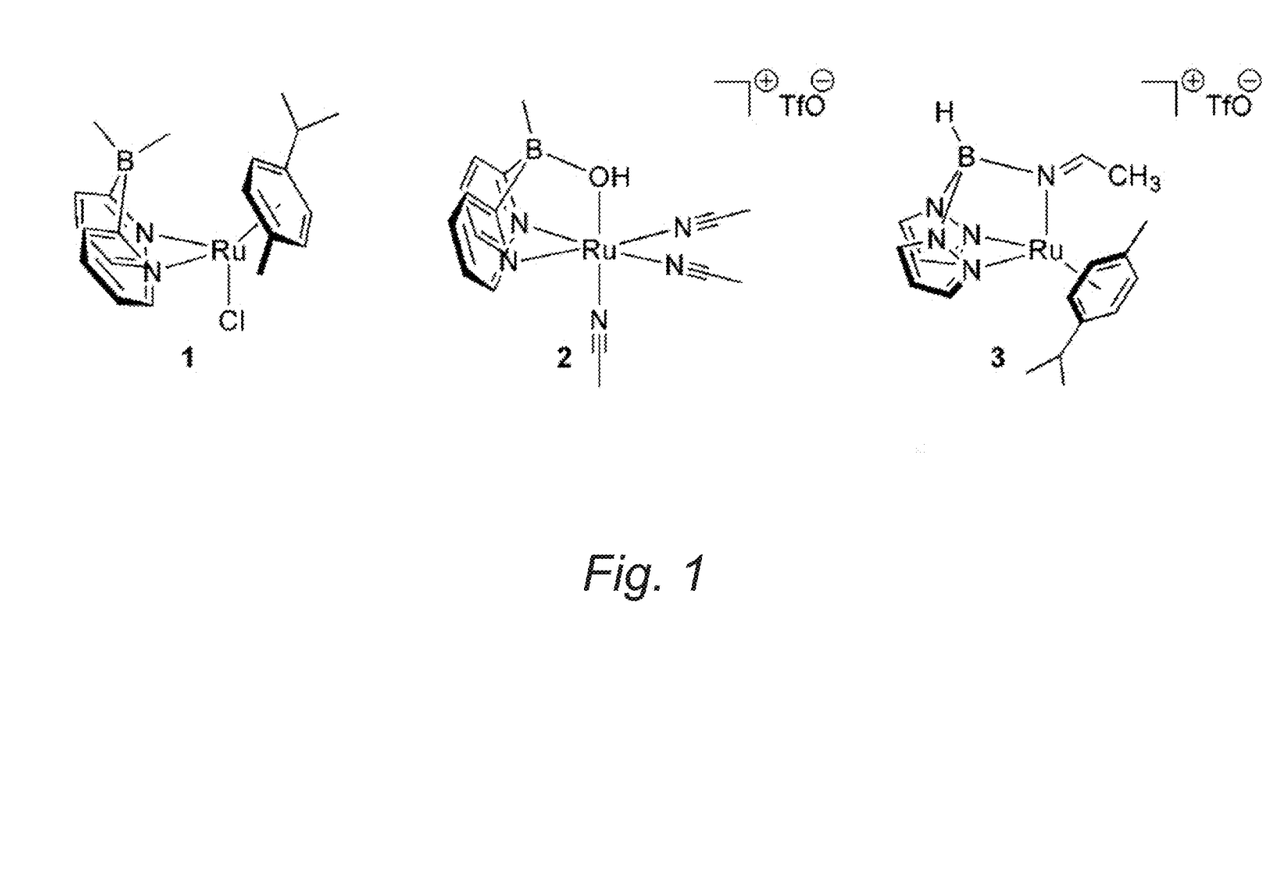
FIG. 1 provides structures of dual site catalysts for hydride manipulation.

As part of our ongoing studies of dual site ruthenium and boron-containing catalysts for the manipulation of hydride groups, we have recently reported a series of [di(pyridyl)borate]ruthenium complexes (1, 2)[1] that exhibit remarkable reactivity in a number of applications,[2] notably including dehydrogenation of ammonia borane.[3] Although they are successful catalysts, these di(pyridyl)dimethylborate-derived complexes are cumbersome to prepare, due largely to dependence on an expensive and reactive BrBMe₂ starting material and high water and oxygen sensitivity of intermediate complexes in their syntheses. Further, despite their catalytic utility, no direct evidence has been collected to give a mechanistic account of the cooperative role, if any, that boron and ruthenium play in the reactive mechanisms of 1 or 2.[4] We suspect this is partially due to the robustness of the bridging μ-OH ligand between the boron and ruthenium centers in 2, which inhibits access to a free borane in catalytic reactions (FIG. 1).

Accordingly, there is a need to develop a strategy to overcome each of these limitations and introduce a new synthesis of primary amines from nitriles.

SUMMARY

In at least one embodiment, a compound having formula I that functions as a catalyst for reducing organic functional groups and, in particular, for reducing nitriles is provided:

(I)

wherein:
$R_1$ are each independently hydrogen, $C_{1-8}$ alkyl, chlorine, bromine, fluorine, or OH;
x is 0 to 3;
$R_2$ is $C_{6-12}$ aryl, $C_{5-12}$ heteroaryl or $C_{1-8}$ alkyl;
$L_1$ are each independently ligands associated with M, each $L_1$ are the same or different; and
a is an integer from 1 to 6; and
M is a transition metal.

In another embodiment, a compound that functions as a catalyst for reducing nitriles has formula II is provided:

(II)

wherein:
$R_1$ are each independently hydrogen, $C_{1-8}$ alkyl, chlorine, bromine, fluorine, or OH;
x is 0 to 3;
$R_2$ is $C_{6-12}$ aryl, $C_{5-12}$ heteroaryl or $C_{1-8}$ alkyl;
$R_3$ are each independently hydrogen, $C_{1-8}$ alkyl, chlorine, bromine, fluorine, or OH;
z is 0 to 4; and
M is a transition metal.

In still another embodiment, a method for reducing a reducible group is provided. The method includes a step of contacting a compound having a cyano group (i.e., R—CN) or aldehyde group (i.e., HCO—R) or ketone group (i.e., RCO—R) with the compound having formula I or II and with a reducing agent (e.g., $NaBH_4$).

BRIEF DESCRIPTION OF THE DRAWINGS

Exemplary embodiments of the present invention will become more fully understood from the detailed description and the accompanying drawings, wherein.

DETAILED DESCRIPTION

Reference will now be made in detail to presently preferred compositions, embodiments, and methods of the present invention which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; "R" groups include H, $C_{1-10}$ alkyl, $C_{2-10}$ alkenyl, $C_{6-14}$ aryl (e.g., phenyl, halo, or $C_{4-14}$ heteroaryl; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application to more fully describe the state of the art to which this invention pertains.

In an embodiment, a compound that functions as a catalyst for reducing nitriles is provided. The compound is generally described by general formula I as follows:

(I)

wherein:
$R_1$ are each independently hydrogen, $C_{1-8}$ alkyl, chlorine, bromine, fluorine, or OH;
x is 0 to 3;
$R_2$ is $C_{6-12}$ aryl, $C_{5-12}$ heteroaryl or $C_{1-8}$ alkyl;
$L_1$ are each independently ligands associated with M, each $L_1$ are the same or different; and
a is an integer from 1 to 6; and
M is a transition metal. In a refinement, the $R_1$ are each independently hydrogen, methyl, ethyl, n-propyl, isopropyl, n-butyl, sec-butyl, or t-butyl. In a further refinement, the $R_1$ are each independently hydrogen. In another refinement, the $R_2$ are each independently hydrogen, methyl, ethyl, n-propyl, isopropyl, n-butyl, sec-butyl, isobutyl, or t-butyl. In still another refinement, the $R_2$ are each independently methyl, ethyl, n-propyl, isopropyl, n-butyl, sec-butyl, isobutyl, or t-butyl. It should be appreciated that when multiple $R_1$ and/or $L_1$ are present, each one is independently one of the choices set forth above.

In another embodiment, a compound that functions as a catalyst for reducing nitriles has formula II is provided:

(II)

wherein:
$R_1$ are each independently hydrogen, $C_{1-8}$ alkyl, chlorine, bromine, fluorine, or OH;
x is 0 to 3;
$R_2$ is $C_{6-12}$ aryl, $C_{5-12}$ heteroaryl or $C_{1-8}$ alkyl;
$R_3$ are each independently hydrogen, $C_{1-8}$ alkyl, chlorine, bromine, fluorine, or OH;
z is 0 to 4; and
M is a transition metal.

In a refinement, the $R_1$ are each independently hydrogen, methyl, ethyl, n-propyl, isopropyl, n-butyl, sec-butyl, isobutyl, or t-butyl. In a further refinement, the $R_1$ are each independently hydrogen. In another refinement, the $R_2$ are each independently hydrogen, methyl, ethyl, n-propyl, isopropyl, n-butyl, sec-butyl, isobutyl, or t-butyl. In another refinement, the $R_2$ are each independently methyl, ethyl, n-propyl, isopropyl, n-butyl, sec-butyl, isobutyl, or t-butyl. In still another refinement, the $R_3$ are each independently hydrogen, methyl, ethyl, n-propyl, isopropyl, n-butyl, sec-butyl, isobutyl, or t-butyl. It should be appreciated that when multiple $R_1$ and/or $R_3$ are present, each one is independently one of the choices set forth above.

In a variation of the compounds described by formulae I and/or II, M is a metal selected from the group consisting of beryllium, magnesium, aluminum, scandium, titanium, vanadium, chromium, manganese, iron, cobalt, nickel, copper, zinc, gallium, germanium, yttrium, zirconium, niobium, molybdenum, technetium, ruthenium, rhodium, palladium, silver, cadmium, indium, tin, antimony, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, iridium, gold, platinum, thallium, lead, bismuth, polonium, thorium, protactinium, uranium, neptunium, and plutonium. In a particularly useful refinement, M is ruthenium. In another particularly useful refinement, M is iridium.

In a variation of the compounds described by formulae I and/or II, the $L_1$ are each independently selected from the group consisting of neutral two electron donor ligands, anionic two electron donor ligands, pi-donor ligands, multidentate ligands, and monodentate ligands. In a refinement, the $L_1$ are each independently selected from the group consisting of substituted or unsubstituted phenyl, carbon dioxide, halide, hydride, nitrate, hydroxide, acetonitrile, pyridine, ammonia, aquo, boryl, and combinations thereof.

In still another embodiment, a method for reducing a reducible functional group is provided. The method includes a step of contacting a compound having a cyano group (i.e., R—CN) or aldehyde group (i.e., HCO—R) or ketone group (i.e., RCO—R) with the compound having formula I or II and with a reducing agent (e.g., $NaBH_4$). In a refinement, the reducing agent is selected form the group consisting of $NaBH_4$, alcohols, and formic acid. In another refinement, the reducible functional group is a $C_{2-12}$ aldehyde and/or a $C_{3-12}$ aldehyde.

A particularly useful catalyst is described by formula 3:

3

Figure 2:
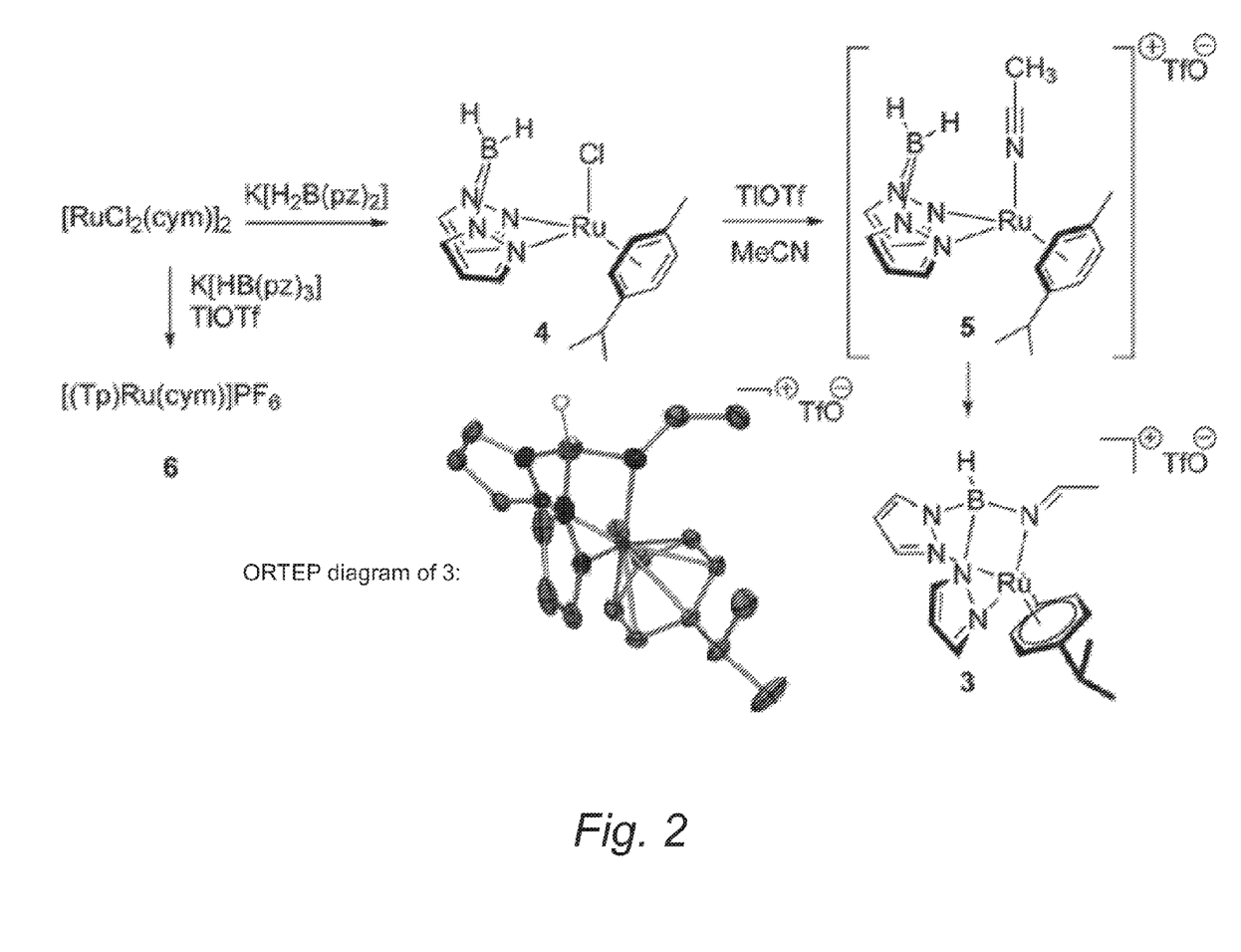
FIG. 2 provides Scheme 1 which illustrates the synthesis of precursor 3 and complex 6, and the molecular structure of 3.

The synthesis of 3 (Scheme 1) proceeds from potassium di(pyrazolyl)borohydride[5-7] and commercially-available (cymene)ruthenium dichloride dimer to give intermediate chloride 4. Although 4 can be isolated, it is easily converted in situ to 3 by treatment with 1 equiv. of thallium (or silver) triflate in nitrile solution. The synthesis proceeds in two smooth steps without the need for materials that are cost-prohibitive or difficult to manipulate: all materials are amenable to handling using standard Schlenk techniques and/or a glove box. 3 can be crystallized using isopropanol and hexanes; its molecular structure was determined by single crystal X-ray diffraction (Scheme 1). The crystal structure of 3 shows the borate ligand bonded to boron in a tetrahedral geometry, which has analogy to the popular tris(pyrazolyl)borohydride (Tp) ligand series.[6-8]

The synthesis of 3 revealed an important insight into the mechanism of its catalytic reactivity. In the conversion of 4 to 3, a hydride is transferred from a ligand B—H group to the coordinated nitrile of 5 in >90% NMR yield (Scheme 1). Contrary to the design concept from which we originally prepared 2,[2] the boron atom in 3 does not behave as a Lewis acid. The structure of 3 shows that addition of the B—H group to the nitrile proceeds in a cis fashion, and NMR evidence reveals that the selectivity for this geometry is exclusive. Thus, it is believed that the mechanism for this reaction involves intramolecular hydride transfer from boron to carbon, rapidly followed by (or concerted with) boron-nitrogen coordination.

The stoichiometric reduction of acetonitrile observed in the synthesis of 3 can be made catalytic by treating 3 with nitrile and sodium borohydride,[9] thus enabling a mild and selective approach to the synthesis of primary amines from nitriles.[10] Known methods for nitrile reduction, e.g. use of excess $LiAlH_4$, borohydride reduction of a nitrilium salt,[11] use of metal hydride reagents,[12] or high-pressure hydrogenation[13] can be incompatible with important synthetic handles, such as aryl bromide and nitro groups.[14] Milder conditions compatible with groups like these require a stoichiometric portion of a borane reagent,[15] which in some cases must be independently prepared. The new catalytic mechanism reported here enables high functional group tolerance while incorporating an inexpensive reducing agent.

Table 1 shows the discovery and optimization of our conditions for nitrile reduction. In the presence of 5 mol % 3, 2.0 equiv. of $NaBH_4$ can reduce 4-trifluoromethylbenzonitrile (7a) to the corresponding benzylamine (8a) in 50% conversion by NMR in 5 hours (entry 1). When 1.0 equiv. of $NaO^tBu$ was added, the analogous reaction reached >90% yield (>95% conversion) in the same time. With no catalyst, the reaction was much slower, reaching completion in 7 days with a 43% overall yield (entry 5). If the Tp-ligated homologue of 3 (6, Scheme 1) is used in this reaction, much of the starting material decomposes under the reaction conditions. This illustrates that the μ-acetimine ligand in 3 plays an essential role in nitrile reduction.

TABLE 1

Optimization of nitrile reduction conditions

| Entry | Catalyst | NaO^tBu | 5 h conversion[a] (%) | NMR yield[b] |
|---|---|---|---|---|
| 1 | 3 | None | 50 | [c] |
| 2 | 3 | 1 equiv. | >95 | >90%, 5 h |
| 3 | 2 | 1 equiv. | 46 | 42%, 245 h |
| 4 | 6 | 1 equiv. | 41 | Trace, 245 h |
| 5 | No catalyst | 1 equiv. | 38 | 43%, 245 h |

[a] Starting material consumption by NMR in 5 hours.
[b] Product formed upon consumption of nitrile and subsequent addition of water.
[c] Not recorded.

TABLE 2

Scope of 3-catalyzed nitrile reduction

| Entry | Nitrile | Conditions | Product | Yield (%) |
|---|---|---|---|---|
| 1 | NC-C6H4-CF3 (7a) | 5 mol% 3, 4 eq. $NaBH_4$, 1 eq. $NaO^tBu$, MeOH, Reflux, 12 h | $H_2N$-CH2-C6H4-CF3 (8a) | 82 |

TABLE 2-continued

Scope of 3-catalyzed nitrile reduction

| Entry | Nitrile | Conditions | Product | Yield (%) |
|---|---|---|---|---|
| 2 |  7b | 5 mol% 3<br>8 eq. NaBH$_4$, 1 eq. NaO$^t$Bu<br>MeOH, Reflux, 12 h |  8b | 87 |
| 3 |  7c | 5 mol% 3<br>4 eq. NaBH$_4$, 1 eq. NaO$^t$Bu<br>MeOH, Reflux, 4 h |  8c | 92 |
| 4 |  7d | 5 mol% 3<br>8 eq. NaBH$_4$, 1 eq. NaO$^t$Bu<br>MeOH, Reflux, 14 h |  8d | 85 |
| 5 |  7e | 5 mol% 3<br>4 eq. NaBH$_4$, 1 eq. NaO$^t$Bu<br>MeOH, Reflux, 8 h |  8e | 80 |
| 6 |  7f | 5 mol% 3<br>4 eq. NaBH$_4$, 1 eq. NaO$^t$Bu<br>MeOH, Reflux, 12 h |  8f | 84 |
| 7 |  7g | 5 mol% 3<br>8 eq. NaBH$_4$, 1 eq. NaO$^t$Bu<br>MeOH, Reflux, 12 h |  8g | 60 |
| 8 |  7h | 5 mol% 3<br>4 eq. NaBH$_4$, 1 eq. NaO$^t$Bu<br>MeOH, Reflux, 8 h |  8h | 64 |

TABLE 2-continued

Scope of 3-catalyzed nitrile reduction

| Entry | Nitrile | Conditions | Product | Yield (%) |
|---|---|---|---|---|
| 9 | 7i (NC-furan) | 5 mol% 3, 4 eq. NaBH$_4$, 1 eq. NaO$^t$Bu, MeOH, Reflux, 8 h | 8i (H$_2$N-C(=O)-furan) | 56 |
| 10 | 7j (NC-thiophene) | 5 mol% 3, 4 eq. NaBH$_4$, 1 eq. NaO$^t$Bu, MeOH, Reflux, 8 h | 8j (H$_2$N-C(=O)-thiophene) | 87 |

The substrate scope of nitriles that can be reduced under our optimized conditions is broad. As shown in Table 2, aromatic, aliphatic, and heterocyclic nitriles are smoothly reduced to amines under optimized conditions. Both electron-poor and electron-rich substrates can be reduced in high yield. For example, in the presence of 5 mol % 3, 4.0 equiv. of NaBH$_4$ can reduce 4-trifluorobenzonitrile 7a to the corresponding benzylamine 8a in 82% isolated yield (entry 1). Electron-rich nitrile 7b can be reduced with a similar facility in 87% yield (entry 2). Even more oxidative nitroarene 7c can be reduced with exclusive selectivity for the nitrile over the nitro group (92%, entry 3). We believe that this startling result is attributable to selective binding and activation of the nitrile over the nitro group by the ruthenium center of the catalyst. Furthermore, we see this as additional evidence showing that nitrile binding to ruthenium is important to the catalytic mechanism.

Despite the highly reducing conditions, an aryl bromide group in nitrile 7d is not derivatized in the course of amine synthesis. This is an important result because aryl bromides such as these are high value substrates for cross-coupling and amination reactions relevant to the synthesis of medicinally relevant compounds.[16] This example further illustrates high-yielding reduction of an alkyl nitrile. Whereas ketone groups are known to react with NaBH$_4$, the reduction of 7e (entry 5) illustrates high-yielding double reduction for the synthesis of amino-alcohol 8e. A similar double reduction is observed in the reaction of cinnamonitrile (7g, entry 7) to give alkyl amine 8g in 60% yield.

Reactions of nitriles appended to aromatic heterocycles afforded complicated results. For example, pyridine 7h is compatible with the conditions and resulted in the formation of aminomethylpyridine 8h in 64% yield (entry 7). By remarkable contrast, more electron-rich heterocycle systems are not reduced. For example, 2-cyanofuran 7i and 2-cyanothiophene 7j are selectively monohydrated as opposed to being reduced. Thus, amides 9i and 9j were isolated as the main products (entries 9 and 10). We suspect that the mechanism for these reactions involves the addition of methanol (solvent) to a ruthenium-coordinated nitrile, and that the amide products are formed upon aqueous work-up. We do not currently have a proposal to account for the selectivity of hydration versus reduction.

Figure 3:
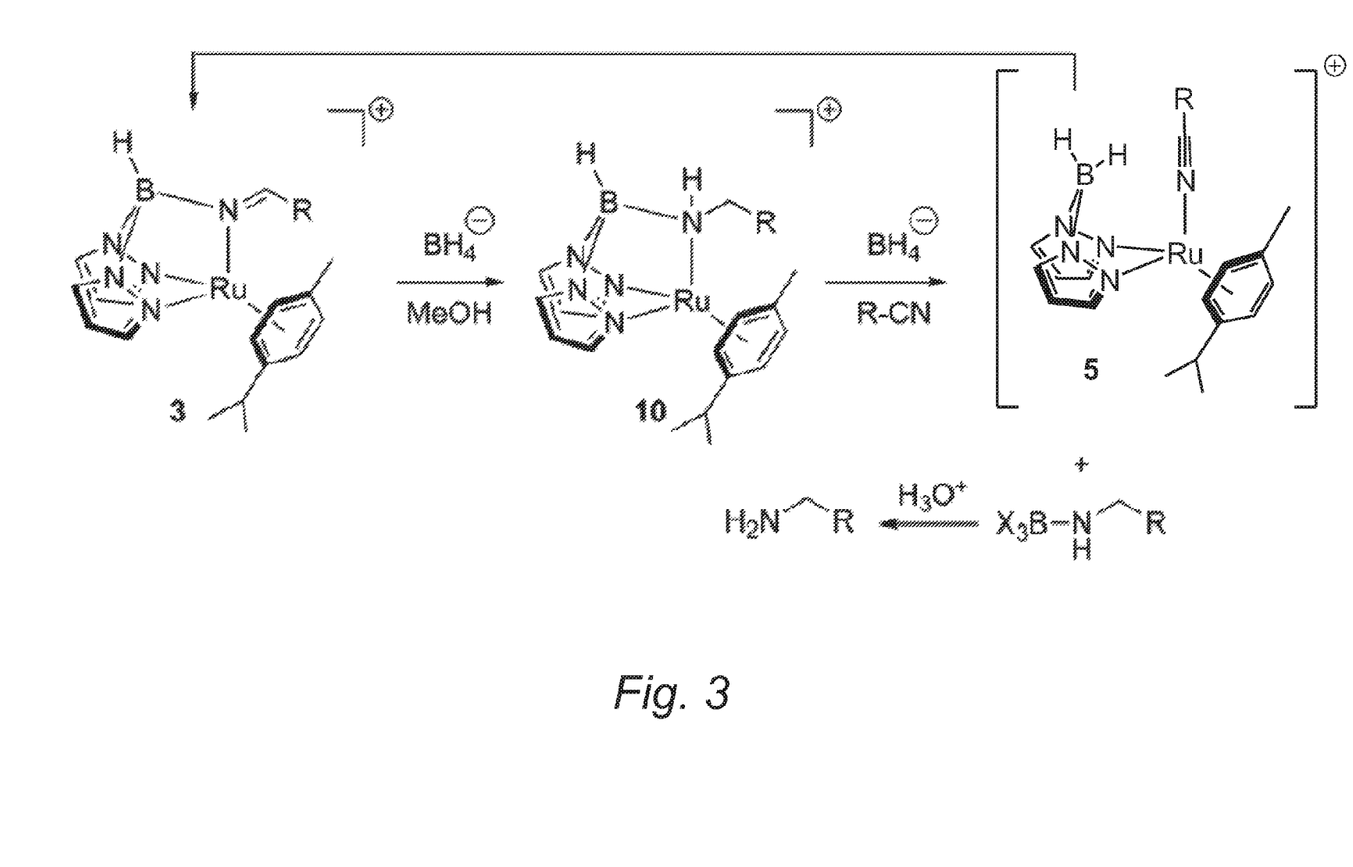
FIG. 3 provides Scheme 2 which illustrates a mechanistic template for nitrile reductions.

According to the insight gained from the stoichiometric synthesis of 3 from 4, we propose the following template mechanism for catalysis (Scheme 2). We suspect that the bridging imine of 3 is reduced by borohydride to produce the amine product. We do not have direct evidence for the intermediacy of 10; however, treatment of 3 with a stoichiometric portion of NaBH$_4$ in methanol-d$_4$ results in clean desymmetrization of cymene and pyrazole C—H groups of the catalyst, consistent with the formation of diastereotopic protons, as expected with the pyramidalization of the bridging nitrogen ligand. Still, the intermediacy of 10 remains a proposal because we have not established the kinetic role of this transient material.

It is proposed that the bridging amine ligand is replaced by an incoming substrate, and the borohydride group of 5 is regenerated by a hydride from NaBH$_4$, although the details of these steps are not known. It is observed by $^1$H-coupled $^{11}$B NMR spectroscopy that treatment of 3 with a stoichiometric portion of NaBH$_4$ in methanol-d$_4$ results in the formation of (MeO)$_4$B$^-$, unreacted BH$_4^-$ and a catalyst doublet, which indicates that a (pz)$_2$BH$_2$ intermediate, if formed, is transient. Thus, it is suspected that X in Scheme 2 is methoxide. $^1$H NMR studies of the working catalyst reveal that once ligated, the reductions of the nitrile groups and imine groups are very facile. Thus, the rate-determining step could be amine for nitrile substitution in the conversion of 10.

Figure 4:
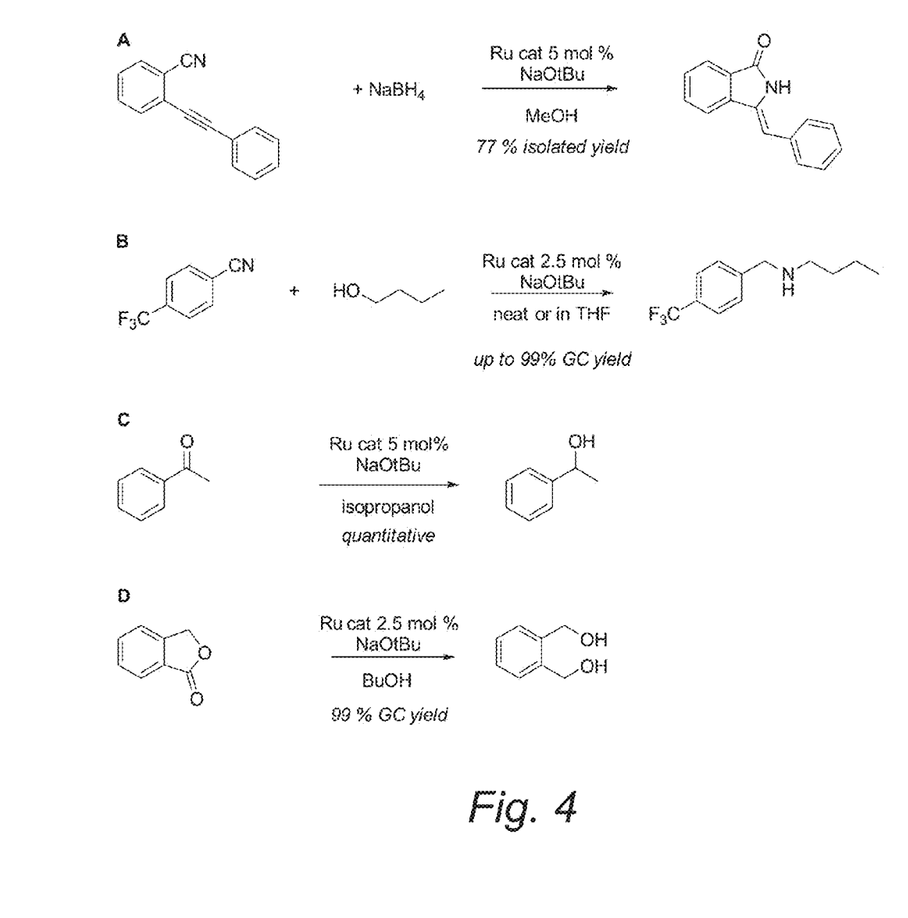
FIG. 4 provides synthetic applications for the catalysts of the invention.

Additional applications of the claimed catalyst are illustrated in FIG. 4. Line A shows the application of the claimed catalyst in tandem reduction/intramolecular cyclization reaction, thus to enable a synthetic approach to isoindolinones. Line B illustrates an important feature of the catalyst, which is that the sodium borohydride reducing agent can be substituted with an alcohol. This particular example shows tandem nitrile reduction and amine alkylation, both mediated by butanol in the presence of the claimed catalyst. Lines C and D of FIG. 4 show the utility of the claimed catalyst in the reduction of ketone and ester (lactone) groups, respectively. Each of these cases illustrate an alcohol as the stoichiometric reducing agent.

In conclusion, embodiments of the invention provide conveniently prepared homologues of the successful di(pyridyl) borate-ligated ruthenium complexes. The new catalytic scaffold shows comparable reactivity to the old one in several key reactions and confers new reactivity to the cooperative ruthe- nium-boron catalytic motif by enabling selective and high yielding nitrile reduction under mild conditions. Furthermore, this platform has yielded new insight into the cooperative reactivity of ruthenium and boron by showing a plausible scenario of how these two centers can work together, respectively, as an activating group (ruthenium) and a hydride donor (boron).

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

1. B. L. Conley and T. J. Williams, *J. Am. Chem. Soc.*, 2010, 132, 1764-1765.
2. B. L. Conley and T. J. Williams, *Comments Inorg. Chem.*, 2011, 32, 195-218.
3. B. L. Conley, D. Guess and T. J. Williams, *J. Am. Chem. Soc.*, 2011, 133, 14212-14215.
4. Z. Lu, B. Malinoski, A. V. Flores, D. Guess, B. L. Conley and T. J. Williams, *Catalysts*, 2012, 2, 412-421.
5. *Scorpionates: The Coordination of Polypyrazolylborate Ligands*, ed. S. Trofimenko, Imperial College Press, London, 1999.
6. For recent reviews of organometallic chemistry of poly(pyzalolyl)borate ligated complexes, see: (a) L. M. Caldwell, *Adv. Organomet. Chem.*, 2008, 56, 1-94; (b) M. Lail, K. A. Pittard and T. B. Gunnoe, *Adv. Organomet. Chem.*, 2008, 56, 95-153; (c) E. Becker, S. Pavli and K. Kirchner, *Adv. Organomet. Chem.*, 2008, 56, 155-197; (d) I. R. Crossly, *Adv. Organomet. Chem.*, 2008, 56, 199-321.
7. R. J. Abernethy, A. F. Hill, M. K. Smith and A. C. Willis, *Organometallics*, 2009, 28, 6152-6159.
8. S. Bhambri and D. A. Tocher, *J. Chem. Soc., Dalton Trans.*, 1997, 3367-3372.
9. A ruthenium-ligated acetonitrile was reduced by NaBH$_4$, however the system produced unidentified products. 13: L. F. Rhodes and L. M. Venanzi, *Inorg. Chem.*, 1987, 26, 2692-2695.
10. M. Vogt, A. Nerush, M. A. Iron, G. Leitus, Y. Diskin-Posner, L. J. W. Shimon, Y. Ben-David and D. Milstein, *J. Am. Chem. Soc.*, 2013, 135, 17004-17018.
11. R. F. Borch, *Chem. Commun.*, 1968, 442-443.
12. For example, stoichiometric portions of $Ni^{II}$, $Co^{II}$, $Os^{IV}$, $Ir^{III}$, $Pt^{II}$, are known to mediate nitrile and nitro group reduction in the presence of excess NaBH$_4$. Y. Suzuki, Y. Miyaji and Z. Imai, *Tetrahedron Lett.*, 1969, 52, 4555-4558.
13. For selected examples, see: H. Paul, S. Bhaduri and G. K. Lahiri, *Organometallics*, 2003, 22, 3019-3021; P. A. Chase, T. Jurca and D. W. Stephan, *Chem. Commun.*, 2008, 1701-1703; R. Reguillo, M. Grellier, N. Vautravers, L. Vendier and S. Sabo-Etienne, *J. Am. Chem. Soc.*, 2010, 132, 7854-7855; X. Miao, C. Fischmeister, C. Bruneau, J.-L. Dubois and J.-L. Couturier, *Chem Sus Chem*, 2012, 5, 1410-1414.
14. P. Magnus, N. Sane, B. P. Fauber and V. Lynch, *J. Am. Chem. Soc.*, 2009, 131, 16045-16047.
15. D. Haddenham, L. Pasumansky, J. DeSoto, S. Eagon and B. Singaram, *J. Org. Chem.*, 2009, 74, 1964-1970.
16. For selected reviews of utilization of aryl bromides in medicinal synthesis, see: J. Hassan, M. Se'vignon, C. Gozzi, E. Schulz and M. Lemaire, *Chem. Rev.*, 2002, 102, 1359-1470; D. Alberico, M. E. Scott and M. Lautens, *Chem. Rev.*, 2007, 107, 174-238; G. Zeni and R. C. Larock, *Chem. Rev.*, 2006, 106, 4644-4680; J.-P. Corbet and G. Mignani, *Chem. Rev.*, 2006, 106, 2651-2710; F.-S. Han, *Chem. Soc. Rev.*, 2013, 42, 5270-5298; Y. Aubin, C. Fischmeister, C. M. Thomas and J.-L. Renaud, *Chem. Soc. Rev.*, 2010, 39, 694-711; G. P. McGlacken and L. M. Bateman, *Chem. Soc. Rev.*, 2009, 38, 2447-2464; T. R. M. Rauws and B. U. W. Maes, *Chem. Soc. Rev.*, 2012, 41, 2463-2497.

What is claimed is:

1. A compound having formula I:

(I)

wherein:
R$_1$ are each independently hydrogen, C$_{1-8}$ alkyl, chlorine, bromine, fluorine, or OH;
x is 0 to 3;
R$_2$ is C$_{6-12}$ aryl, C$_{5-12}$ heteroaryl or C$_{1-8}$ alkyl;
L$_1$ are each independently ligands associated with M, each L$_1$ are the same or different; and
a is an integer from 1 to 6; and
M is a transition metal.

2. The compound of claim 1 having formula II:

(I)

wherein:
R$_1$ are each independently hydrogen, C$_{1-8}$ alkyl, chlorine, bromine, fluorine, or OH;
x is 0 to 3;
R$_2$ is C$_{6-12}$ aryl, C$_{5-12}$ heteroaryl or C$_{1-8}$ alkyl;
R$_3$ are each independently hydrogen, C$_{1-8}$ alkyl, chlorine, bromine, fluorine, or OH;
z is 0 to 4; and
M is a transition metal.

3. The compound of claim 1 having the following formula:

4. The compound of claim 1 wherein M is a metal selected from the group consisting of beryllium, magnesium, aluminum, scandium, titanium, vanadium, chromium, manganese, iron, cobalt, nickel, copper, zinc, gallium, germanium, yttrium, zirconium, niobium, molybdenum, technetium, ruthenium, rhodium, palladium, silver, cadmium, indium, tin, antimony, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, iridium, gold, platinum, thallium, lead, bismuth, polonium, thorium, protactinium, uranium, neptunium, and plutonium.

5. The compound of claim 1 wherein M is ruthenium.

6. The compound of claim 1 wherein the $L_1$ are each independently selected from the group consisting of neutral two electron donor ligands, anionic two electron donor ligands, pi-donor ligands, multidentate ligands, and monodentate ligands.

7. The compound of claim 1 wherein the $L_1$ are each independently selected from the group consisting of substituted or unsubstituted phenyl, carbon dioxide, halide, hydride, nitrate, hydroxide, acetonitrile, pyridine, ammonia, aquo, boryl, and combinations thereof.

8. The compound of claim 1 wherein the $R_1$ are each independently hydrogen, methyl, ethyl, n-propyl, isopropyl, n-butyl, sec-butyl, isobutyl, or t-butyl.

9. The compound of claim 2 wherein the $R_3$ are each independently hydrogen, methyl, ethyl, n-propyl, isopropyl, n-butyl, sec-butyl, isobutyl, or t-butyl.

10. The compound of claim 1 wherein the $R_2$ are each independently methyl, ethyl, n-propyl, isopropyl, n-butyl, sec-butyl, isobutyl, or t-butyl.

11. A method comprising:
contacting a compound having a reducible functional group with a metal-containing compound having formula I or II and a reducing agent:

the reducible functional group being a cyano group, aldehyde group, and/or ketone group, wherein:
$R_1$ are each independently hydrogen, $C_{1-8}$ alkyl, chlorine, bromine, fluorine, or OH;

$R_2$ is $C_{6-12}$ aryl, $C_{5-12}$ heteroaryl or $C_{1-8}$ alkyl;

$R_3$ are each independently hydrogen, $C_{1-8}$ alkyl, chlorine, bromine, fluorine, or OH;

$L_1$ are each independently ligands associated with M, each $L_1$ are the same or different;

a is an integer from 1 to 6;

x is 0 to 3;

z is 0 to 4; and

M is a transition metal.

12. The method of claim 11 wherein the reducing agent is selected form the group consisting of $NaBH_4$, alcohols, and formic acid.

13. The method of claim 11 wherein the reducible functional group is a cyano group.

14. The method of claim 11 wherein the reducible functional group is a $C_{2-12}$ aldehyde and/or a $C_{3-12}$ aldehyde.

15. The method of claim 11 wherein M is a metal selected from the group consisting of beryllium, magnesium, aluminum, scandium, titanium, vanadium, chromium, manganese, iron, cobalt, nickel, copper, zinc, gallium, germanium, yttrium, zirconium, niobium, molybdenum, technetium, ruthenium, rhodium, palladium, silver, cadmium, indium, tin, antimony, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, iridium, gold, platinum, thallium, lead, bismuth, polonium, thorium, protactinium, uranium, neptunium, and plutonium.

16. The method of claim 11 wherein M is ruthenium.

17. The method of claim 11 wherein the $L_1$ are each independently selected from the group consisting of neutral two electron donor ligands, anionic two electron donor ligands, pi-donor ligands, multidentate ligands, and monodentate ligands.

18. The method of claim 11 wherein the $L_1$ are each independently selected from the group consisting of substituted or unsubstituted phenyl, carbon dioxide, halide, hydride, nitrate, hydroxide, acetonitrile, pyridine, ammonia, aquo, boryl, and combinations thereof.

19. The method of claim 11 wherein the $R_1$ are each independently hydrogen, methyl, ethyl, n-propyl, isopropyl, n-butyl, sec-butyl, isobutyl, or t-butyl.

20. The method of claim 11 wherein the $R_2$ and the $R_3$ are each independently methyl, ethyl, n-propyl, isopropyl, n-butyl, sec-butyl, isobutyl, or t-butyl.

* * * * *